United States Patent
Fuhr

(10) Patent No.: US 6,440,285 B1
(45) Date of Patent: Aug. 27, 2002

(54) METHOD AND DEVICE FOR MICRO PARTICLES POSITIONING IN FIELD CAGES

(75) Inventor: Günter Fuhr, Berlin (DE)

(73) Assignee: Evotec Oai AG, Hamburg (DE)

( * ) Notice: Subject to any disclaimer, the term of this patent is extended or adjusted under 35 U.S.C. 154(b) by 0 days.

(21) Appl. No.: 09/319,172

(22) PCT Filed: Dec. 12, 1997

(86) PCT No.: PCT/EP97/07001

§ 371 (c)(1),
(2), (4) Date: Aug. 2, 1999

(87) PCT Pub. No.: WO98/28604

PCT Pub. Date: Jul. 2, 1998

(30) Foreign Application Priority Data

Dec. 20, 1996  (DE) .......................................... 196 53 661

(51) Int. Cl.⁷ ............................................... G01N 27/26
(52) U.S. Cl. ....................... 204/457; 204/450; 204/600; 204/643
(58) Field of Search ................................ 204/450, 457, 204/458, 547, 600, 608, 609, 643

(56) References Cited

U.S. PATENT DOCUMENTS 5,084,157 A    1/1992  Clark et al. .................. 204/609

FOREIGN PATENT DOCUMENTS

| DE | 4034697  | 5/1992  |
| DE | 4400955  | 6/1995  |
| DE | 19500660 | 6/1996  |
| DE | 19500683 | 6/1996  |
| EP | 0453780  | 10/1991 |
| WO | 9422583  | 10/1994 |

OTHER PUBLICATIONS

Hu et al. ( "Oscillating characteristics of charged levitated particles under external electric field in a quadrupole levitaiton trap", J. Electrost (1993), 30, 29–38), Month Unknown.*
Muller et al. (High–frequency electric–field trap fo micron and submicron particlces, Nuovo Cimento Soc. Ital. Fis., D (1995), 17D940, 425–32), Apr.*
CAPLUS abstract of Fuhr (DE 19500683 A1).*
Derwent abstract of Fuhr (DE 19500683 A1).*
Huang, y. et al. J. Phys. D: Appl. Phys., vol. 26, 1993, pp. 1528–1535, Month Unknown.
Wang, X. –B et al. J. Phys. D: Appl. Phys., vol. 26, 1993, pp. 1278–1285, Month Unknown.
Pethig, Roland et al. J. Phys. D: Appl. Phys., vol. 24, 1992, pp. 881–888, Month Unknown.
Washizu, Masao et al. IEEE Trans. Ind. Appl., vol. 26, No. 2, 1990, pp. 352–358, Mar./Apr.
Block, Steven M. et al. In Nature, vol. 338, 1989, pp. 514–518, Apr.
Masuda, Senichi et al. IEEE Trans. Ind. Appl., vol. 24, No. 2, 1988, pp. 217–222, Mar./Apr.
Ashikin, A. et al. In Nature, vol. 24, No. 2, 1988, pp. 217–222, Dec.
Fuhr, Gunter et al. In Naturwissenschaften, vol. 81, 1994, pp. 525–528, Month Unknown.
Ashkin, A. et al. In Optics Lett., vol. 11, 288 (1986).
Eigen, M. et al. In Proc. Natl. Acad. Sci. USA, vol. 91, 1994, pp. 5740–5747, Jun.

* cited by examiner

Primary Examiner—T. Tung
Assistant Examiner—Alex Noguerola

(57) ABSTRACT

In a method for positioning or controlling the motion of an object in a multi-electrode arrangement for forming a field cage, the basic potentials for driving the electrodes are modulated with drive potentials in such a way that the object position in the field cage changes in relation to a predetermined position or path. A device for arranging objects at predetermined positions in a multi-electrode arrangement has a switching device by which basic potentials, produced by generator means, can be modulated according to predetermined drive potentials (FIG. 1).

10 Claims, 2 Drawing Sheets

METHOD AND DEVICE FOR MICRO PARTICLES POSITIONING IN FIELD CAGES

This application is the national phase under 35 U.S.C. §371 of PCT International Application No. PCT/EP97/07001 which has an International filing date of Dec. 12, 1997 which designated the United States of America.

FIELD OF THE INVENTION

The invention concerns a method for controlling the position or the motion of objects in field cages and a device for performing such a method.

BACKGROUND OF THE INVENTION

In numerous biological, medical, pharmacological and physical or chemical engineering processes one is interested in holding microscopic particles, especially biological cells or their constituents, latex particles or other microbeads, as precisely as possible in position or moving them along a certain path. One known method of retaining biological cells is that of growing them on a solid substrate, which can then be set with the required accuracy; for example, with reference to a means of measurement. The drawback of this technique is that of creating a mechanical contact with the substrate surface and the generally difficult separation of this contact, after performing a measurement. Furthermore, this technique is restricted to retaining objects and unsuitable for moving them along a certain path.

Another known technique is that of positioning objects in free fluids by optical means. With so-called laser tweezers, it is possible to hold particles in free solutions with micrometer accuracy or to shift them in a predetermined manner (see A. Ashkin et al. "Observation of a single-beam gradient force optical trap for dielectric particles" in Optics Lett., vol. 11, p 288 (1986)). This so-called optical trapping presents drawbacks, because the particle within the trapping laser beam is subjected to thermal collisions and thus slight, random shifts in position. Furthermore, optical measurements on retained particles are limited in scope because of interference with the laser beam. The latter restriction is avoided in the manipulation of particles in electric microfield cages where the objects can be retained or moved by polarization forces (see G. Fuhr et al. "Radio-frequency microtools for particle and live cell manipulation" in Naturwissenschaften, vol. 81, p 528 (1994), or: DE-OS 195 00 660)). Nevertheless, here too there are thermally related shifts in the position of the retained or moved particles that can make high-resolution or high-sensitivity measurements as in correlation spectroscopy (see M. Eigen et al. "Sorting single molecules, application to diagnostics and evolutionary biotechnology" in Proc. Nat. Acad. Sci. USA, volume 91, p 5740 (1994)), difficult or even impossible.

It is a known principle where the particle to be retained is made to vibrate in the required position to enable locally triggered measurement with reduced interference from thermal collisions. For this purpose the retained particle in the required position is made to vibrate by sound (especially ultrasonic sound) or periodic movements of solution so that there is a certain periodic movement at the required position. The correspondingly modulated measurement signal shows an improved signal/noise ratio.

This vibration technique exhibits the following disadvantages however. The forces for creating the vibration act indirectly, through the surrounding fluid, on the retained particle. So not only the particle but also the surrounding fluid is moved, thus reducing the reproducibility of particle positioning. Moreover, unwanted rotary motion, difficult to control, can appear as a result of this indirect action of forces. Certain applications where motion of the surrounding fluid is undesired cannot be implemented. Finally, mechanical stress can occur on the retained particle, which is a special problem with living biological objects.

The known techniques do not allow one to influence the positioning of a particle along a required path. But there is also a requirement for control of motion beyond what is possible with the above mentioned vibration technique.

SUMMARY OF THE INVENTION

Accordingly, it is the object of the invention to provide an improved method of positioning objects with electric field cages and to propose a device for implementing the said method, extending the usability of the above mentioned vibration technique and creating new possibilities of control.

This object is solved by a method with the features of patent claim 1 and a device with the features of patent claim 9. Advantageous embodiments of the invention are defined in the dependent claims.

The invention is based on the idea of departing from the use of forces acting indirectly through motion of the fluid when positioning by superimposing vibration or using other means to control motion, and instead focuses on moving the object a periodically or periodically through the effect of forces that act directly on the retained object but not on the surrounding fluid (suspension, solution). For this purpose electric potentials on electrodes of a multi-electrode configuration are used to create an open or closed field cage. Such potentials are superimposed with drive or control potentials so that the position of the field minimum, where the particular object is to be found, changes in relation to a required object position. The required object position can be either a certain location within a closed field cage or a path within an open field cage (duct structure or the like). A periodic change of position means that the retained particle is conducted periodically on a path around the required, predetermined object position. The shape of this superimposed trajectory can be chosen as desired and can include a vibratory motion in relation to one, two or three spatial axes, circular, elliptical, essentially rectangular, or even in more complex paths. The time pattern of the spatially periodic motion can itself exhibit periodic modulation. An aperiodic change of position means that the retained particle is led away from a predetermined object position on a certain path.

If the required object position is formed by a path within an open field cage, the moving of the object along the required path can be produced by appropriate selection of the driving of the electrodes with base potentials and/or by a fluid flow.

A device according to the invention possesses an electrode arrangement that can be driven by a combination of high-frequency generators and a switching device. The switching device is adapted to superimpose a drive potential on the potential (basic potential) of one or more electrodes so that the amplitude, the frequency and/or the phase of the resulting total potential alters.

The invention produces the following advantages, especially in the positioning of objects that are freely supported with surrounding fluids in field cages.

The positioning or moving of the object is performed without mechanical contact. The objects are not exposed to any disturbing mechanical stress, so in particular live biological cells and the like are not damaged. There are no restrictions at all with regard to further manipulation or measurement of the retained objects. Common optical methods of measurement can be employed while avoiding interference problems. Motion of the objects about the required location or on the required path can be created in complex reproducible manner, differing from harmonic vibratory processes. The superimposed motion of the objects can be controlled or programmed in a predetermined way. There is a unique relation between the form of the drive potentials and the object motions that are produced, so no feedback or observation of the moved object is necessary for control purposes. Finally, the invention can be used with any electrode arrangements to create field cages, independently of the concrete electrode form or configuration.

Preferred uses for the methods and devices according to the invention are correlation spectroscopy, especially for detecting fluorescent molecules on the surface of submicrometer or micrometer particles and/or cells, pharmacological and medical diagnostic applications and/or evolution biotechnology. Especially suitable as means of detection are the method of fluorescence correlation spectroscopy (WO 94/16313) as well as other, particularly confocal fluorescence techniques, as proposed in the publication WO 96/13744 and the European patent application 96116373.0. This latter application suggests a method for analyzing samples by repeated measurement of the number of photons per predetermined time interval of the electromagnetic radiation, in particular light, that is emitted, scattered and/or reflected by the particles in the sample, and determination of the distribution of the number of photons in the particular time intervals, whereby the distribution of the molecular intensity of the particles obtained from the distribution of the number of photons.

BRIEF DESCRIPTION OF THE DRAWINGS

Embodiments of the invention will be explained in the following with reference to the attached drawings, showing

DETAILED DESCRIPTION OF THE PREFERRED EMBODIMENTS

Figure 1:
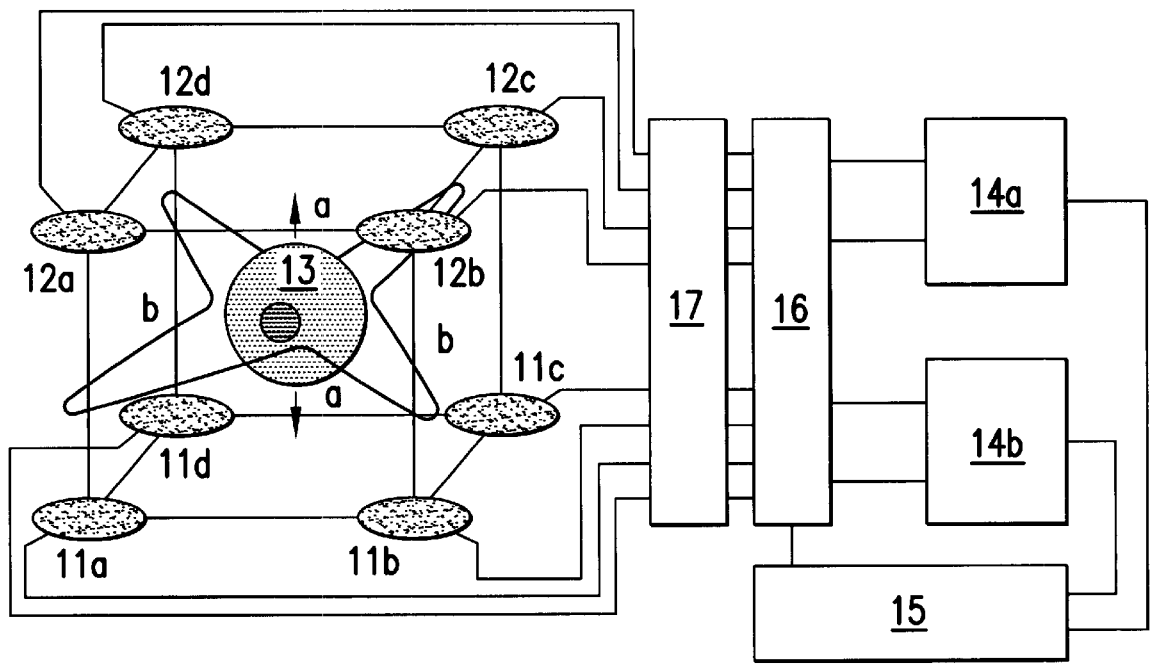
FIG. 1: schematic perspective of a three-dimensional field cage with a block diagram of a driving circuit according to an embodiment of the invention.

The individual features of the method according to the invention or of the driving circuit, explained below with reference to the embodiments of the invention, are not restricted to these embodiments. It is possible for a skilled person to select modifications of the embodiments, as a function of the application, especially in terms of amplitude, frequency and phase of the basic and drive potentials of the electrodes.

For an implementation of the method according to the invention, electrode arrangements are used as known from microsystems technique for creating field cages and which are preferably produced by the methods of semiconductor technology. In the case of two-dimensional electrode arrangements, the electrodes are formed on a chip surface with characteristic size in the nm to $\mu$m region. Three-dimensional electrode arrangements can consist of two planar, two-dimensional arrangements joined by using structured spacers to form ducts, reservoirs or other spaces permitting a flow.

Basic electric potentials are applied to microelectrodes (cross-section 50 nm to several $\mu$m, length depending on application) so that a certain electric field is created in the inner space formed between the microelectrodes. The microsystem, especially the inner space, is filled with the carrier fluid or the latter flows through it. If there is a suspended particle (an object to be retained or moved) in the carrier fluid, it is polarized by the effect of the electric field. If the electrodes are driven by high-frequency signals (MHz range) or if the external conductivity (of the carrier fluid) is higher than the mean internal conductivity of the particle or particles, they are pressed away from the electrodes into the inner space to a field minimum. In the region of the field minimum the particles are retained freely suspended in the carrier fluid (closed field cage). If the electrodes are arranged and driven so that a potential wall only forms in one direction, but motion of the particles is possible in another direction, especially through the effect of a fluid flow, then the particle in the field cage can move in a certain direction (open field cage).

The basic potentials of the electrodes are chosen so that the particle is located at a predetermined position in the field cage. This predetermined position is the location of the field minimum in the closed field cage or the path (trajectory) in the open field cage. According to the invention, the actual field minimum is displaced from the predetermined position by periodic and ordered superimposition of drive potentials on the basic potentials (or alteration of the basic potentials according to the drive potentials). This displacement can occur with characteristic times of us to min. Depending on the inertia of the objects and the viscosity of the solution, the retained particles track the field minimum and thus move on predetermined paths in relation to the required position or trajectory.

Depending on the number of electrodes and how they are driven, the superimposed motion can be a simple vibration on one axis or a more complex path in space. The invention allows motion in all directions. The invention also enables to compensate for random or unwished rotating motion of a particle by the application of a compensating potential. The compensating potentials comprise suitable rotating or moving, electric high-frequency fields.

The electrodes are driven by RF generators to produce the basic potentials. The generator output signals are attenuated, shifted in phase and/or altered in frequency periodically or aperiodically (especially in response to an actuating signal that indicates a certain object position). These changes determine the particular drive potentials under the effect of which the superimposed motion of the retained particles occurs. The drive potentials can be modulated in amplitude, phase or frequency. Combinations of these modes of modulation are also possible.

The electrodes are driven through a fast switching device, in particular a multiplexer arrangement. To implement complex motion patterns, the multiplexer arrangement is preferably computer-controlled and programmable.

As an example FIG. 1 shows a quadrupole arrangement with eight electrodes 11a–11d and 12a–12d in the form of a cube. An electric field with a field minimum at the center of the cube is formed in the known manner by applying high-frequency alternating voltages to the electrodes. The limits of the field cage are shown schematically by the lines between the electrodes. In the inner space of the electrode arrangement there is a carrier fluid with a suspended dielectric particle 13 (eg a latex particle of a few μm diameter or a biological cell). The dielectric particle is polarized so that negative influence charges point to the next negative electrode (and vice versa). In this way an octupole is influenced on the particle and the particle is shifted to the field minimum.

The righthand part of FIG. 1 shows a block diagram of a driving circuit for the electrodes. The driving circuit comprises at least one RF generator connected to a multiplexer device 16 acting as the fast switching device. In the case illustrated here there are two RF generators 14a, 14b. The number of RF generators will be chosen according to the application, ie whether two, three, four or more phase or frequency offset signals are to be used to drive the electrodes. Between the multiplexer device 16 and the electrodes there is a calibration element 17 that acts with the multiplexer for fast alteration of the amplitude, the frequency and/or the phase of each potential. The multiplexer device 16 and the calibration element 17 will preferably be controlled by a computer or it will be possible to set them in a predetermined way. The signals of the RF generators 14a, 14b are split by the multiplexer device 16 and the calibration element 17 in the way explained with reference to Table 1 so that a field cage is created between electrodes 11a–11d, 12a–12d.

Table 1 represents the driving of the electrodes of the octupole with basic potentials of a certain amplitude (in the range from 0.1 to 100 V) and a certain frequency (MHz range). To form a closed field cage, the basic potentials of the individual electrodes differ through the opposing phase. A two-phase alternating field and a four-phase rotating field are formed, the relative phases corresponding essentially to the values indicated in Table 1.

According to the invention, the field minimum generated at the center of gravity of the field cage by driving the electrodes according to Table 1 is moved so that a particle in the field minimum follows the trajectory (a) or (b) for example (see FIG. 1). Trajectory (a) is a vibration in a spatial direction (two movements per period), while trajectory (b) is a complex, star-shaped path in the field cage (eight movements per period). Any other trajectories can be implemented depending on how the electrodes are driven.

The mentioned movements of the field minimum are produced by superimposing drive potentials, examples of whose parameters are listed in Table 2, on the basic potentials according to Table 1.

The first six lines of Table 2 refer to the trajectory (a) shown in FIG. 1. Two lines refer in each case to the two oppositely directed movements 1, 2 of the vibration, and there are three possibilities of driving to produce this, ie by influencing amplitude, frequency or phase. The phases φ1, φ2 of the third possibility (lines 5, 6) are arbitary choices to form a fixed difference. The difference will preferably be φ1–φ2=180°, but other differences are also possible. The same applies to driving by amplitude and frequency. Lines 1 and 2, 3 and 4 show respective examples.

The bottom eight lines of Table 2 refer to the chronological sequence of the eight motions to create the star-shaped trajectory (b) when the drive potentials are influenced in amplitude. Again the amplitudes stated here are just examples.

A skilled person will recognize that the method of the invention is not restricted to the examples for generation of drive potentials in Table 2. Instead, mixtures of drive potentials influenced in amplitude, frequency and phase are possible. In every case, to create a superimposed movement in relation to a required object position, it is a matter of selecting the drive potentials and their sequence so that a field cage is formed with a potential wall reduced in one direction, whereby the direction of this weakening of the field cage will change periodically in relation to the required object position or path.

The field minimum in the field cage according to FIG. 1 is moved by driving the electrode arrangement with potentials formed by superimposition on the basic potentials according to Table 1 and drive potentials according to Table 2. The captured particle follows this movement because it will attempt to assume a position of minimum energy.

The controller 15 outlined in FIG. 1 can, in the simplest case, be replaced by a multivibrator that alternately halves the amplitudes of the upper electrode level 12 and the lower electrode level 11. This produces the trajectory (a).

The drive potentials (signal modulation as in Table 2) or the periods of the superimposed motions exhibit characteristic time constants of the order of μs to min. The path diameters or deflections produced by shifting the field minimum can be in the range between 50 nm and several μm. More complicated trajectories than (a) and (b) can be generated through the appropriate drive potentials.

Figure 2:
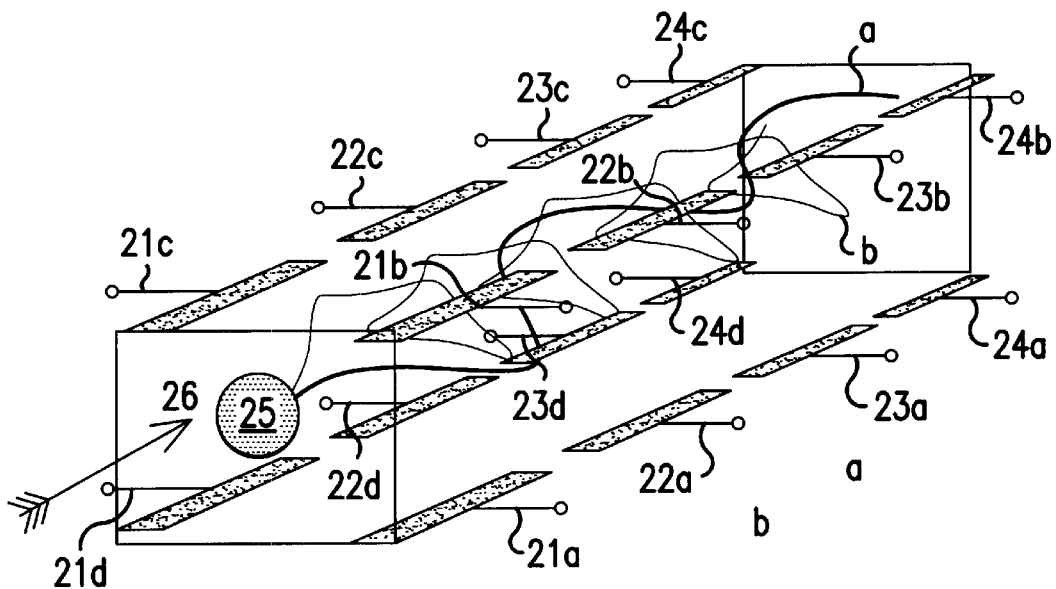
FIG. 2: schematic perspective of an open field cage to illustrate particle paths modified according to the invention.

FIG. 2 is an example of an open field cage consisting of a linear sequence of several quadrupoles 21a–21d, 22a–22d, 23a–23d, 24a–24d. The electrode arrangement forms a duct in which a particle 25 is conducted by a fluid flow 26. The particle trajectories (a) and (b), shown as examples, can be produced by driving the electrodes appropriately. Table 3 shows how the electrodes are driven for the trajectory (a) indicated by a bold continuous line. In a first step (first line) the electrodes are driven so that the field cage exhibits a weakening in the region of the electrodes 21a–d in the direction of the plane formed by the electrodes 21a and 21b. For this purpose the potential of the latter electrodes is reduced. In a second step the motion is reversed by weakening the field cage on the opposite side (reduction of potential on electrodes 22c and 22d). This continues in an analogous fashion.

Advantageously it is not essential to know where a particle is located. Just periodic repetition of the signal sequences given as examples in Table 3 can produce the required motion. Preferably the repetition is at a frequency whose reciprocal is about 1/10 of or greater than the time that the particle takes to pass through a quadrupole arrangement.

Figure 3:
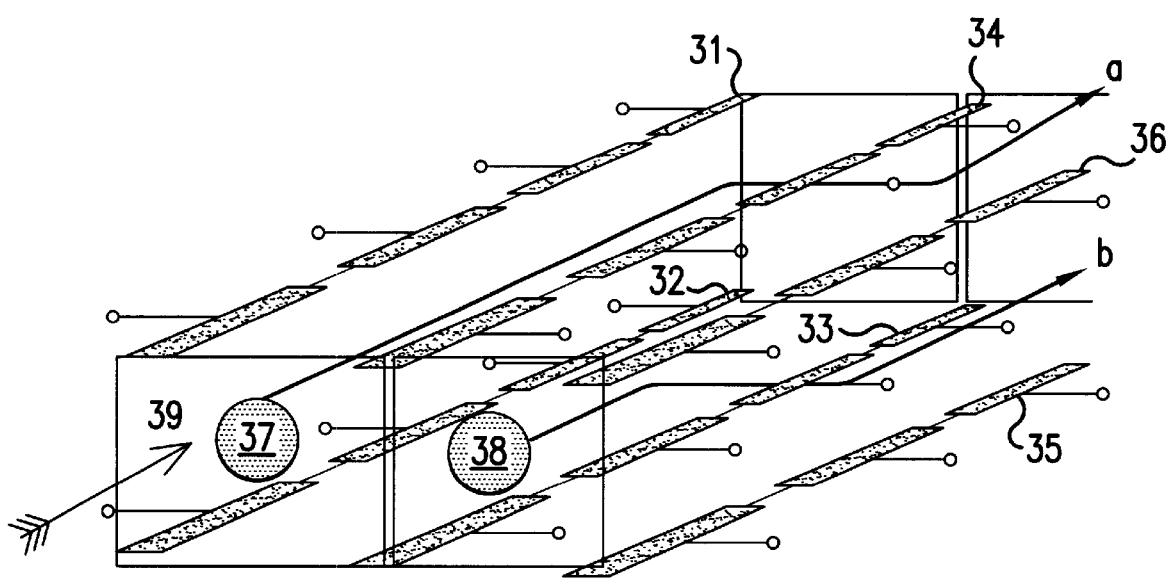
FIG. 3: schematic perspective of an electrode arrangement for two adjacent, open field cages.

An electrode arrangement according to FIG. 3 is intended for coupling particles into and out of a particle stream. The electrodes 31 through 36, driven singly or in groups, are arranged in several rows and a free suspension can flow through them, in any direction but preferably parallel to the electrode rows.

The trajectories (a) and (b) can be produced by driving protocols of analogous form to the examples explained above. Particles can be separated and sorted by adding staggered means of connection (multi-duct connection).

TABLE 1

Phase φ when driving eight electrodes according to FIG. 1 with basic potentials to form a closed field cage with one field minimum (basic setting)

| Basic control | Period of basic signal | El. 11a | El. 11b | El. 11c | El. 11d | El. 12a | El. 12b | El. 12c | El. 12d |
|---|---|---|---|---|---|---|---|---|---|
| Alternating field | 1 | 0° | 180° | 0° | 180° | 180° | 0° | 180° | 0° |
|  | 2 | 180° | 0° | 180° | 0° | 0° | 180° | 0° | 180° |
| Rotating field | 1 | 0° | 90° | 180° | 270° | 180° | 270° | 0° | 90° |
|  | 2 | 90° | 180° | 270° | 0° | 270° | 0° | 90° | 180° |
| 4 phases | 3 | 180° | 270° | 0° | 90° | 0° | 90° | 180° | 270° |
|  | 4 | 270° | 0° | 90° | 180° | 90° | 180° | 270° | 0° |

TABLE 2

Driving of electrodes according to FIG. 1 to generate trajectories (a) and (b)

| Trajectory | Motion | El. 11a | El. 11b | El. 11c | El. 11d | El. 12a | El. 12b | El. 12c | El. 12d |
|---|---|---|---|---|---|---|---|---|---|
| a | 1 | Ampl. V | Ampl. V | Ampl. V | Ampl. V/4 | Ampl. V | Ampl. V/4 | Ampl. V/4 | Ampl. V/4 |
|  | 2 | Ampl. V/4 | Ampl. V/4 | Ampl. V/4 | Ampl. V/4 | Ampl. V | Amp. V | Ampl. V | Ampl. V |
| a | 1 | Freq. f | Freq. f | Freq. f | Freq. f | Freq. f/10 | Freq. f/10 | Freq. f/10 | Freq. f/10 |
|  | 2 | Freq. f/10 | Freq. f/10 | Freq. f/10 | Freq. f/10 | Freq. f | Freq. f | Freq. f | Freq. 1 |
| a | 1 | Phase φ1 | Phase φ2 | Phase φ1 | Phase φ2 | Phase φ1 | Phase φ1 | Phase φ1 | Phase φ1 |
|  | 2 | Phase φ2 | Phase φ2 | Phase φ2 | Phase φ2 | Phase φ1 | Phase φ2 | Phase φ1 | Phase φ2 |
|  | 1 | Ampl. V/4 | Ampl. V | Ampl. V | Ampl. V | Ampl. V/4 | Ampl. V | Ampl. V | Ampl. V |
|  | 2 | Ampl. V | Ampl. V | Ampl. V | Ampl. V | Ampl. V | Ampl. V | Ampl. V | Ampl. V |
|  | 3 | Ampl. V | Ampl. V/4 | Ampl. V | Ampl. V | Ampl. V | Ampl. V/4 | Ampl. V | Ampl. V |
|  | 4 | Ampl. V | Ampl. V | Ampl. V | Ampl. V | Ampl. V | Ampl. V | Ampl. V | Ampl. V |
|  | 5 | Ampl. V | Ampl. V | Ampl. V/4 | Ampl. V | Ampl. V | Ampl. V | Ampl. V/4 | Ampl. V |
|  | 6 | Ampl. V | Ampl. V | Ampl. V | Ampl. V | Ampl. V | Ampl. V | Ampl. V | Ampl. V |
|  | 7 | Ampl. V | Ampl. V | Ampl. V | Ampl. V/4 | Ampl. V | Ampl. V | Ampl. V | Ampl. V/4 |
|  | 8 | Ampl. V | Ampl. V | Ampl. V | Ampl. V | Ampl. V | Ampl. V | Ampl. V | Ampl. V |

TABLE 3

Phase φ when driving electrodes according to FIG. 2.

| Trajectory | Motion | Electrode 21 | | | | Electrode 22 | | | | Electrode 23 | | | | Electrode 24 | | | |
|---|---|---|---|---|---|---|---|---|---|---|---|---|---|---|---|---|---|
|  |  | a | b | c | d | a | b | c | d | a | b | c | d | a | b | c | d |
| a | 1 | V/4 | V/4 | V | V | V | V | V | V | V | V | V | V | V | V | V | V |
|  | 2 | V | V | V | V | V | V | V/4 | V/4 | V | V | V | V | V | V | V | V |
|  | 3 | V | V | V | V | V | V | V | V | V/4 | V/4 | V | V | V | V | V | V |
|  | 4 | V | V | V | V | V | V | V | V | V | V | V | V | V | V | V/4 | V/4 |

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A method for moving at least one dielectric particle in a fluidic microsystem, said fluidic microsystem comprising fluid containing said dielectric particle and also an electrode arrangement with a plurality of electrodes to which basic electric high frequency potentials are applied for influencing positive and negative charges in the particle by subjecting the particle to polarization forces and for forming a field cage with at least one field minimum at a predetermined position, thereby moving the particle, the method comprising:

controlling at least one electrode for modulating at least one of the basic potentials by at least one drive potential in such a way that the position of an actual field minimum, where the particle in the field cage is located, changes in relation to the predetermined position.

2. The method according to claim 1, wherein a closed field cage is formed by the basic potentials and the change in the position of the actual field minimum is periodic in time and space.

3. The method according to claim 2, wherein the at least one drive potential is formed by modulation of at least one of the amplitudes, the phases and the frequencies of the at least one modulated basic potential.

4. The method according to claim 3, wherein the actual field minimum changes along a closed path.

5. The method according to claim 1, wherein the change of the actual field minimum occurs in a time range that is substantially longer than the reciprocal frequency of the frequencies of the basic potential.

6. The method according to claim 1, wherein the basic potentials are adapted to form an open field cage which has a potential wall in one direction and which allows particle motion in another direction, and the at least one drive potential is selected so that the at least one particle moves in relation to a predetermined path.

7. The method according to claim 1, wherein the at least one drive potential follows time patterns for periodic alteration of the position of the actual field minimum.

8. The method according to claim 1, wherein a plurality of particles are positioned in an electrode arrangement.

9. A fluidic microsystem comprising:
   an electrode arrangement including a plurality of electrodes, adapted to form a field cage for at least one dielectric particle by the influence of electric polarization forces, said field cage including at least one field minimum; and
   generator means, including a switching device, for applying basic electric high-frequency potentials to the electrodes and for modulating at least one of the basic potentials according to at least one predetermined drive potential, wherein a fluid can be filled or can flow between the electrodes of the electrode arrangement.

10. The fluidic microsystem according to claim 9, wherein the switching device is formed by a multiplexer for selective driving of the electrodes.

* * * * *